United States Patent [19]
McColskey et al.

[11] Patent Number: 5,587,534
[45] Date of Patent: Dec. 24, 1996

[54] WALL THICKNESS AND FLOW DETECTION APPARATUS AND METHOD FOR GAS PIPELINES

[75] Inventors: Joseph D. McColskey, Broomfield; William P. Dube, Denver; Christopher M. Fortunko, Boulder; Raymond E. Schramm, Thornton; Martin C. Renken, Boulder, all of Colo.; Cecil M. Teller, II; Glenn M. Light, both of San Antonio, Tex.

[73] Assignee: The United States of America as represented by the Secretary of Commerce, Washington, D.C.

[21] Appl. No.: 330,592

[22] Filed: Oct. 28, 1994

[51] Int. Cl.⁶ .................................................. G01N 29/10
[52] U.S. Cl. ................................. 73/623; 73/592; 73/598
[58] Field of Search .............................. 73/623, 622, 639, 73/638, 598, 633, 644, 592

[56] References Cited

U.S. PATENT DOCUMENTS

| | | |
|---|---|---|
| 3,409,897 | 11/1968 | Bosselarr et al. . |
| 3,413,653 | 11/1968 | Wood . |
| 3,439,527 | 4/1969 | Rohrer . |
| 3,478,576 | 11/1969 | Bogle . |
| 3,592,967 | 7/1971 | Harris . |
| 3,810,384 | 5/1974 | Evans . |
| 3,850,028 | 11/1974 | Thompson et al. . |
| 4,092,868 | 6/1978 | Thompson et al. . |
| 4,104,922 | 8/1978 | Alers et al. . |
| 4,189,944 | 2/1980 | Day et al. .................................. 73/623 |
| 4,218,923 | 8/1980 | Triplett et al. ............................. 73/623 |
| 4,285,243 | 8/1981 | Collingwood ............................. 73/623 |
| 4,372,151 | 2/1983 | Muraview et al. . |
| 4,416,145 | 11/1983 | Goodman et al. . |
| 4,485,668 | 12/1984 | Hudson et al. . |
| 4,522,063 | 6/1985 | Ver Nooy . |
| 4,641,529 | 2/1987 | Lorenzi et al. ............................ 73/623 |
| 4,987,769 | 1/1991 | Peacock et al. . |
| 5,333,501 | 8/1994 | Okada et al. . |

FOREIGN PATENT DOCUMENTS

| | | | |
|---|---|---|---|
| 31962 | 2/1986 | Japan ........................................ 73/623 |
| 231260 | 9/1988 | Japan ........................................ 73/623 |

OTHER PUBLICATIONS

"Non–Destructive Testing", vol. II, Apr. 23–28, 1989, Proceedings of the 12th World Conference on Non–Destructive . . . , edited by J. Boogaard and G. M. van Dijk.

"Gas–Coupled Ultrasonics For The Inspection Of Pipes In Natural Gas Delivery Systems", 1981, prepared by Fortunko et al., p. 10.

"Gas–Coupled Acoustic Microscopy In The Pulse–Echo Mode" 1993 Ultrasonics Symposium, by C. M. Fortunko, W. P. Dube, & J. D. McCloskey, NIST, Materials Reliability Division, Boulder, CO.

"Assessment of Technology For Detection of Stress . . . ", prepared by Nondestructive Eval.Science & Tech. Division, SW Research Institute, 1994.

Translation JP 39162.

*Primary Examiner*—Hezron E. Williams
*Assistant Examiner*—Nashmiya Ashraf
*Attorney, Agent, or Firm*—Patent Law Offices of Rick Martin, P.C.

[57] ABSTRACT

A new ultrasonic method for measuring wall thickness and detecting material flaws in natural-gas pipelines, risers, and similar structures. The method is inherently suitable for the task, because it relies on the use of the natural gas as the coupling fluid for transmitting the probing ultrasonic signals into and out of the pipe wall. Furthermore, the method facilitates the operation of the inspection from the inside of the pipe. An experimental apparatus used to demonstrate the technical feasibility of this approach and provide experimental and theoretical evidence that support the claims is described. Significantly, it is shown that by the use of a diplexer, the same transducer can be used to generate and detect the probing ultrasonic signals. The same configuration is used in commercial ultrasonic inspection of oil pipelines where oil is the coupling fluid; but until now this method could not be used in natural gas pipelines due to the low specific acoustic impedance of natural gas.

11 Claims, 7 Drawing Sheets

WALL THICKNESS AND FLOW DETECTION APPARATUS AND METHOD FOR GAS PIPELINES

FIELD OF INVENTION

The present invention relates to the detection of wall thickness and flaws in natural gas pipelines. The device packages an ultrasonic transducer in a pipeline pig, and has an electronics component with a large dynamic range.

BACKGROUND OF THE INVENTION

Ultrasonic inspection is a standard method to assess the integrity of large-diameter oil pipelines. However, similar methods applied to natural-gas pipelines present a considerably greater challenge. Gas is a poor coupling agent for the probing ultrasonic signals emanating from the transducer to the pipe wall. Natural gas exhibits a very low specific acoustic impedance (300 Rayls for methane at 1 bar) compared to oil (1.5 MRayls and higher). Consequently, large ultrasonic-signal transmission losses occur at the transducer/gas and pipe-wall interfaces. To circumvent this obstacle, past exploratory developments included the use of a liquid-filled wheel, electromagnetic-acoustic-transducer (EMAT), and liquid-slug technologies. While prototypes of high-speed, in-line inspection systems employing such principles exist, all exhibit serious operational shortcomings that prevent their wide spread commercial exploitation.

Experimental results demonstrate the technical feasibility of an alternative approach to the important problem of high-speed, in-line ultrasonic inspection of natural-gas pipelines. The present invention teaches the operation of a gas-coupled ultrasonic inspection system in the classic pulse-echo configuration to detect pipeline flaws and observe wall-thickness variations. Experimental results demonstrate good signal-to-noise characteristics. Therefore, the present invention provides the enabling technology for high-speed, in-line ultrasonic inspection systems for natural-gas pipelines, risers, and similar structures. A brief summary of the related prior art follows below.

U.S. Pat No. 3,409,897 (1968) to Bosselarr et al. discloses a method for detecting and locating leaks in pipelines—mainly oil pipelines. The device detects the ultrasonic noise generated by the escape of fluid from the pipeline. This device does not address wall thickness in pipelines.

U.S. Pat. No. 3,413,653 (1968) to Wood discloses a method of detecting leaks in pipelines. The device uses a geometry of seals to detect the noise of a pipeline breach via an ultrasonic detector upstream and downstream of the pig. This method also uses a magnetic detector to detect welds. Using the three detectors it is possible to differentiate leaks, welds, and background noise from each other.

U.S. Pat. No. 3,439,527 (1969) to Rohrer discloses an apparatus to test gas mains characterized by a high pressure chamber formed by seals on a pig like device. The high pressure chamber has a microphone connected to earphones at ground level. The earphones are used to listen for the noise of leaks in the gas main. This device is not used in pipelines, and does not address wall thickness.

U.S. Pat. No. 3,478,576 (1969) to Bogle discloses a pipeline pig having an upstream and downstream detector and a delaying means to synchronize the received signals. This method accentuates the signal generated from leaks and diminishes non-point source noise.

U.S. Pat. No. 3,592,967 (1971) to Harris discloses a leak detector to detect the ultrasonic signal generated by leaks. This device is passive, not oriented to gas pipelines, and does not address wall thickness.

U.S. Pat. No. 3,810,384 (1974) to Evans discloses a device for ultrasonically measuring the wall thickness of pipelines and detecting cracks in pipelines via a pig. This device is for pipelines containing a suitable coupling fluid. Typical of such coupling fluids are the hydrocarbons (i.e. gasoline, oil, liquefied petroleum gas, or water) which surrounds the transducer and interior of the pipe wall.

U.S. Pat. No. 4,372,151 (1983) to Muraviev et al. discloses an automatic fault locating apparatus. The apparatus detects the leading edge of a pressure drop wave generated by a breach of a pipeline. This device consists of a permanently connected sensor.

U.S. Pat. No. 4,416,145 (1983) to Goodman et al. discloses a leak detector for containers as well as mechanical faults (i.e. worn bearings). The device detects the ultrasonic signals from two sources. One is the frequency shift of the signal from an ultrasonic driver. The second is from the sound made by the bursting of bubbles created by a liquid which is applied over the surface of the container after it is pressurized.

U.S. Pat. No. 4,485,668 (1984) to Hudson et al. discloses a method to detect leaks in pressurized pipes by passing a transducer through the pipe to detect leaks. The leak is detected via an above-ground receiver.

U.S. Pat. No. 4,522,063 (1985) to Ver Nooy discloses a method of detecting inadequately supported sections or overloaded points in a pipeline including the steps of traversing the interior of the pipeline with an instrumentation pig, sequentially striking or vibrating the wall of the pipeline by means carried by the pig to introduce vibratory signals into the pipeline, receiving said signals from within the pipeline by listening to the sounds generated as a consequence of the striking of the interior wall, and detecting preselected characteristics of received sound which are indicative of unsupported sections or of points of load and stress concentration in the pipeline.

U.S. Pat. No. 4,987,769 (1991) to Peacock et al. discloses a device to permit ultrasonic leak detection, especially in internal combustion engines. An ultrasonic source is housed in a tubular body adapted for attachment to a spark plug aperture in an engine and ultrasonic signals are injected into the engine cylinders. A directional ultrasonic detector is used to detect leakage signals.

U.S. Pat. No. 5,333,501 (1994) to Okada et al. discloses an abnormality monitoring apparatus that has detectors spaced at locations along a pipeline to detect sound waves. The device locates the abnormality by the time of arrival of sounds from the abnormality.

U.S. Pat. No. 3,850,028 (1974) to Thompson et al. discloses an ultrasonic electro magnetic transducer having an alternating current conductor located in the field of a permanent magnet with said conductor defining a serpentine path lying parallel to the surface of a test object to induce eddy currents in the test object flowing in directions transverse to the field of the permanent magnet. Two such transducers are provided and are employed as a transmitter-receiver pair to generate and detect Rayleigh, Lamb, or other elastic waves within the object under test without requiring contact of the transducers with the object.

U.S. Pat. No. 4,104,922 (1978) to Alers et al. discloses an electromagnetic acoustic transducer is provided for ultrasonically inspecting conductive material as the material moves relative to the transducer. A coil is positioned in the field created by a magnet so that the conductors of the coil are transverse to the magnetic field. The coil is located predominantly near the leading side of the magnet where flux is concentrated as the magnet and material move toward each other.

U.S. Pat. No. 4,092,868 (1978) to Thompson et al. discloses an electromagnetic acoustic method and device which are suitable for the in-place inspection of pipelines. A completely self-contained, mobile inspection station is placed inside a pipeline. The station runs through the pipe and transmits Lamb waves within the pipe wall, receives reflected and transmitted portions of the waves, and records the amplitude and phase of the received waves. The recorded information is analyzed to determine the location and nature of discontinuities in the pipe. This method must be used with metal pipes.

Proceedings of the 12th World Conference on Non-Destructive Testing (1989) by Boogaard et al., "*Evaluation of The Techniques Implemented In Commercially Available On-Stream Pipeline Inspection Tools*", summarizes the results of evaluation tests of pipeline inspection tools. This paper considers the capabilities and limitations of the available pipeline inspection techniques. The paper covers the use of ultrasonic pigs and states that "ultrasonic devices function only when a liquid surrounds the sensors". Additionally, the performance deteriorates significantly in crudes containing wax, water, or gas. This reference summarizes the state of the art in 1989.

"*Gas Coupled Ultrasonics For The Inspection Of Pipes In Natural Gas Delivery Systems*", (1991) a proposal to the Gas Research Institute, describes using a laser coupled transducer to generate an ultrasonic wave as practical with a gas-coupled transducer used to detect the signal. However, the proposal concluded that it would not be possible to use the same gas coupled transducer to generate and receive signals.

"*Gas-Coupled Acoustic Microscopy In The Pulse-Echo Mode*", (1993), C. M. Fortunko et al. demonstrates the technical feasibility of a gas coupled scanning acoustic microscope operating in the pulse-echo mode. A high pressure nitrogen or argon environment is used for this microscope. In this experiment coins encapsulated in polymethyl methacrylate (PMMA) were used as subjects. At present, 0.25 mm sub-surface lateral resolutions are attainable at 3 MHz in PMMA and even better performance should be possible at higher frequencies.

"*Assessment of Technology for Detection of Stress Corrosion Cracking in Gas Pipelines*" (1994), prepared for The Gas Research Institute, is an assessment of non-destructive evaluation technology that can be applied to in-line detection of stress-corrosion cracking in natural gas pipelines. The assessment revealed that no single technology has demonstrated that it meets the industry goals for such inspection, but both ultrasonics and electromagnetic methods were found to be candidates for further development. Also assessed were methods of data analysis that may be used to improve signal discrimination. Comparison tables rate the different techniques within each method and a complete bibliography is appended for related reference material.

SUMMARY OF THE INVENTION

The primary object of the present invention is to provide a method to be used in natural gas pipelines to measure the wall thickness of the pipeline.

Another object of this invention is to provide a method to detect flaws—such as cracks, delamination, scaling, and corrosion—in natural gas pipelines.

Yet another object of the invention is to provide the above advantages by the use of a low cost, fast recovery, large dynamic range amplifier. The amplifier achieves the wide dynamic range by the use of a diplexer.

Still yet another object of the invention is to provide ultrasonic probing signals in the natural gas pipeline wall that are normal to the wall (transverse) and that are at a 45° angle to the normal (longitudinal) to the natural gas pipeline wall.

Other objects of this invention will appear from the following description and appended claims, reference being had to the accompanying drawings forming a part of this specification wherein like reference characters designate corresponding parts in the several views.

The ultrasonic-component technologies used in this invention are similar to those employed earlier to demonstrate the technical feasibility of a gas-coupled, pulse-echo scanning acoustic microscope (G-SAM), using argon and nitrogen as the coupling gases. Prior work published less than a year from the filing date herein showed only surface-mapping and through-transmission using a high-pressure, gas-coupled ultrasonic system with focused transducers. See "*Gas Coupled Acoustic Microscopy In The Pulse Echo Mode*" (1993), Fortunko et al.

In contrast to the pulse-echo G-SAM with a focused ultrasonic transducer, this in-line gas pipeline inspection concept uses flat ultrasonic transducers. This is an important distinction. The successful demonstration of the focused ultrasonic transducer does not imply that a flat transducer will be successful. To detect vertical cracks in steel plates and large-radius shells, the present invention aligns the circular-symmetry axis of the transducer at a slight angle $\theta_i$ with respect to the plate-surface normal. Typically an incident angle $\theta_i$ of 4.5° will launch shear waves in steel plates at a refraction angle $\theta_r$ of 45° with respect to the surface normal when nitrogen is the coupling gas. Correspondingly, an incident angle $\theta_i$ of 2.5° would generate and detect longitudinal waves in steel propagating at a refraction angle $\theta_r$ of 45° using nitrogen as the coupling gas. Because sound propagates faster in natural gas than in nitrogen, 460 m/s vs. 330 m/s, the incidence angles would be somewhat larger in natural gas. To measure wall thickness, the transducer symmetry axis is aligned along the normal to the plate or pipe wall.

Until recently, the general belief was that a gas-coupled, pulse-echo ultrasonic inspection concept would not be feasible because signal losses would be unacceptably large due to high absorption in the gas at MHz frequencies and very high signal-reflection losses at the gas-solid interfaces as a result of the specific impedance mismatch there. However, experimental results show that the use of wide-band, well-dampened ceramic transducers, and high-dynamic-range receiver amplifiers can overcome such effects.

The experimental results of this invention also show that high ultrasonic absorption is not among the major obstacles to overcome when designing gas-coupled, pulse-echo ultrasonic systems at MHz frequencies. In fact, the ultrasonic absorption in nitrogen is only 0.72 dB/mm at 2.25 MHz at 0.1 MPa (15 psi) and decreases inversely with pressure. Ultrasonic absorption in natural gas is unknown because of its variable composition. However, methane is the major component of all natural gases, ranging from 79 to 97 mole percent. Ultrasonic absorption constants of pure methane are well known, both experimentally and theoretically. At 2.25 MHz and 1 bar, the absorption coefficient in pure methane is approximately 0.62 dB/mm. However, actual losses may be significantly greater because of excess absorption caused by molecular-relaxation effects in other constituents.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

DESCRIPTION OF THE PREFERRED EMBODIMENT

Previously electromagnetic acoustic transducers were proposed to excite and detect the probing ultrasonic signals in pipelines. Such transducers require small separations, typically 1 mm, between the transducer face and pipe wall. This invention enables the transducer pipe wall separation distance to be increased to greater than 10 mm. This is a big advantage due to pipeline roughness, steps and weld beads. Additionally, the electromagnetic acoustic transducer requires the pipe wall be metal. The present invention is compatible with pipe walls of metal, plastic, or ceramic. The present invention is compatible with the power supply requirements and signal processing schemes presently used in liquid coupled ultrasonic inspection systems.

Figure 1:
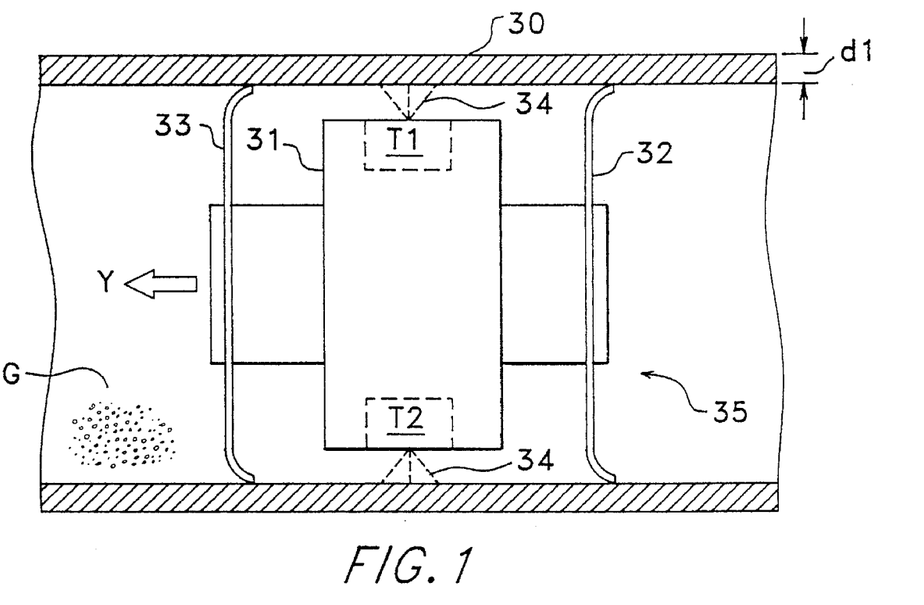
FIG. 1 is a schematic of a cross sectional view of an ultrasonic inspection system mounted on a pig traveling in a natural gas pipeline.

FIG. 1 illustrates the best mode for the practical implementation of the method of this invention.

The instrumentation 31 is on an inspection pig 35 that moves through a pipeline 30 in the direction of flow Y of the gas G. The ultrasonic inspection signals 34 from transducers T1, T2 measure the thickness dl of the pipeline 30 and any flaws (not shown) which may be present in the pipeline 30. To maintain internal spacing and to propel the inspection pig 35 down the pipeline 30, the inspection pig 35 is equipped with seals 32 and 33.

FEASIBILITY DEMONSTRATION

Figure 2:
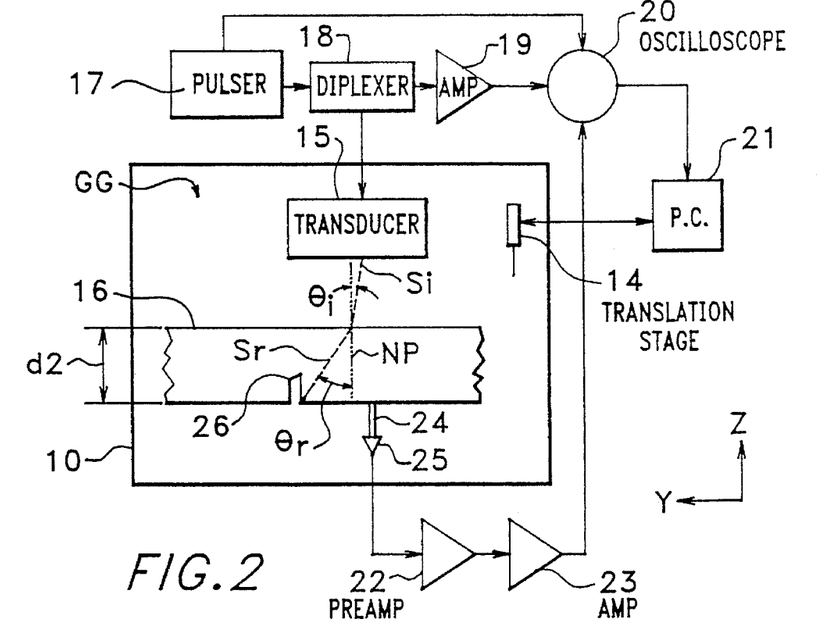
FIG. 2 is a schematic of a feasibility demonstration inside a pressure vessel.

FIG. 2 shows the block diagram of the experimental setup developed at NIST to study ultrasonic-wave propagation phenomena in high-pressure gases. The evaluation of various inspection ultrasonic Non-destructive Testing (NDT) concepts is also disclosed. The setup uses a cylindrical pressure vessel 10, 305 mm (12 in) in diameter and 610 mm (24 in) in length. The pressure vessel 10 can accommodate a variety of gases at pressures up to 10 MPa (1500 psi) and has appropriate feed-throughs for sample and transducer-motion control, signal handling, and pressure and temperature monitoring. Inside the vessel 10, translation stages 14 with multiple degrees of freedom manipulates both the transducer 15 and sample 16. Four position-adjustment motors are located in the translation stages 14 to manipulate the Z coordinate of the sample and X, Y, and $\theta_i$, coordinates of the pulse-echo transducer 15. The X coordinate (not shown) is into the plane of the drawing. The coordinate $\theta_i$ is the angle in the sagittal plane between the transducer symmetry axis and plate-surface normal.

TRANSDUCERS AND ELECTRONICS

A commercial piezoelectric-ceramic transducer 15, 13 mm (0.5 in) in diameter, generates and receives the probing ultrasonic signals $S_i$, $S_r$. The transducer used in this experiment was the Parametrics V306. However, other transducers may be used. The pulse echo transducer 15, mounted at an angle $\theta_i$, transmits an ultrasonic signal $S_i$ into the gas couplant. When the ultrasonic signal $S_i$ reaches the steel plate 16 it is reflected inside the steel plate 16 as ultrasonic signal $S_r$ at an angle $\theta_r$. To detect vertical cracks in steel plates and large radius shells, the present invention aligns the incidence angle $\theta_i$ of the sensor 15 with respect to the plate 16 surface normal NP such that the angle of refraction $\theta_r$ inside the plate 15 is 45°. To measure wall thickness d2 the ultrasonic signal $S_i$ is aligned along the normal NP of the plate 16 and $\theta_i = \theta_r = 0°$. The transducer 15 exhibits a center frequency of 2.25 MHz when operated in water. However, in gas the center frequency is somewhat lower. This may be caused by the frequency-dependent attenuation of sound in the gas. To generate, detect, and condition the ultrasonic signals, the following components are used: a commercial square-wave pulser 17 with 8 kW available peak power at 400 V, a special magnetic diplexer circuit 18, and a high-input-impedance receiver amplifier 19 with 64 dB dynamic range and 60 MHz bandwidth. For the purpose of this feasibility demonstration commercial devices from Ritec, Inc. were used. The amplifier 19 is the Ritec Broadband Receiver Model BR-640. The pulser 17 is the Ritec Square Wave Pulser Model SP-801. The diplexer 18 is the Ritec Diplexer RD-H. It is to be understood that the invention is not limited to the above devices. Manual, stepped attenuators (not shown) control the output pulse available-power levels of pulser 17 and receiver-amplifier gains of amplifier 19. A 400-Ms/s, 8-bit digital storage oscilloscope (DSO) 20 is used to record the signal waveforms. A dedicated personal computer 21 controls the feasibility demonstration.

Figure 3:
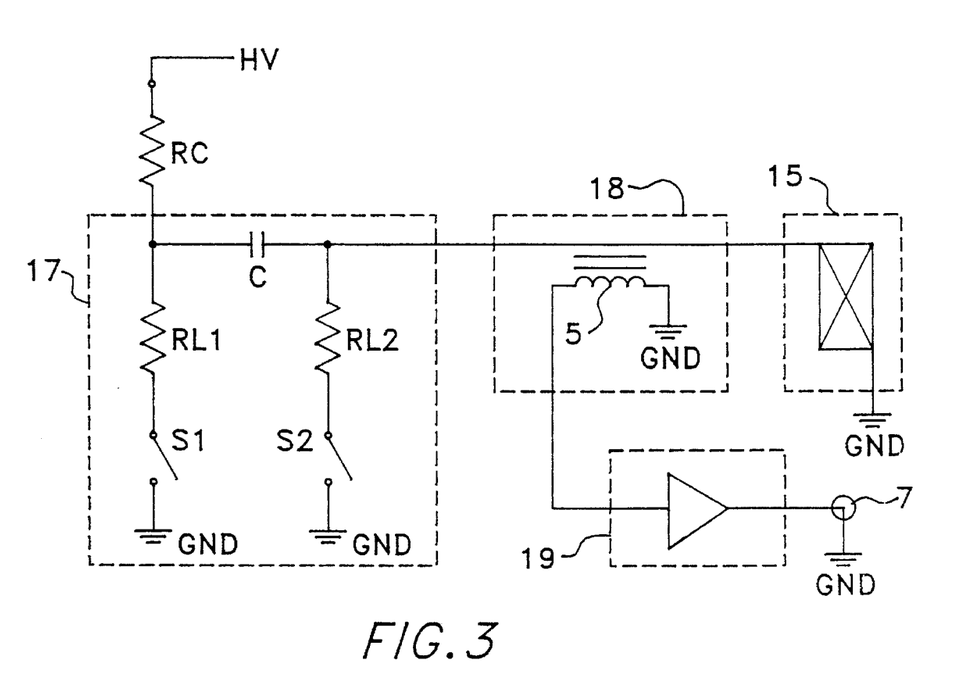
FIG. 3 is a more detailed view of the diplexer and associated electronics of FIG. 2.

FIG. 3 shows a more detailed block diagram of the pulser 17, diplexer 18, amplifier 19, and transducer 15 of FIG. 2. The topology of FIG. 3 forms a particularly effective pulse echo circuit.

The square-wave ultrasonic pulser 17 is implemented using a large storage capacitor C and two semiconductor switches $S_1$ and $S_2$. In addition the series resistors $R_{L1}$ and $R_{L2}$ are employed to establish the output impedance. The storage capacitor C is charged from the high voltage input HV through the resistors $R_C$, $R_{L2}$, and switch $S_2$ to ground GND. Switch $S_2$ is then opened. The electrical pulse which drives the transducer 15 is now generated by first closing switch $S_1$, then closing switch $S_2$. The switch $S_2$ remains in the closed position until the next ultrasonic pulse. This unique feature of the circuit shown in FIG. 3 permits the utilization of a particularly effective diplexer 18 [transmit/receive (T/R) switch] design and helps to reduce the transducer 15 ringdown time. The diplexer 18 is implemented using a broadband transformer 5 which increases the transducer input-impedance level. This feature is helpful in minimizing the noise factor (NF) of the receiver amplifier 19 circuit.

The function of the diplexer 18 is to allow the large ultrasonic pulse to drive the transducer 15. The core of the transformer 5 in the diplexer 18 saturates with the large signal thus protecting the amplifier 19 from harm. Then, when the echo of the ultrasonic pulse returns through the transducer 15, the transformer 5 is out of saturation and allows the small echo signal to return through the amplifier 19 to the output 7.

Although the circuit topology illustrated in FIG. 3 is not efficient in terms of energy utilization, it provides a significant improvement over traditional designs in terms of S/N performance and transducer/preamplifier recovery characteristics.

As shown in FIG. 2, there is a back face transducer 24, directly coupled to the back surface of the flat-plate specimen 16. This is a commercial pin transducer, 1.4 mm in diameter, to provide ultrasonic-beam diagnostics and aid in alignment. Because transducers of this type inherently exhibit very small capacitances (typically 20 pF) compared to the total capacitance of the coaxial cable (nearly 300 pF here) it has a special very-low-noise, voltage-mode preamplifier 25 attached. Another amplifier 23 and preamplifier 22 are in line with the back face transducer 24 to get a signal level suitable for the digital oscilloscope 20.

Figure 4:
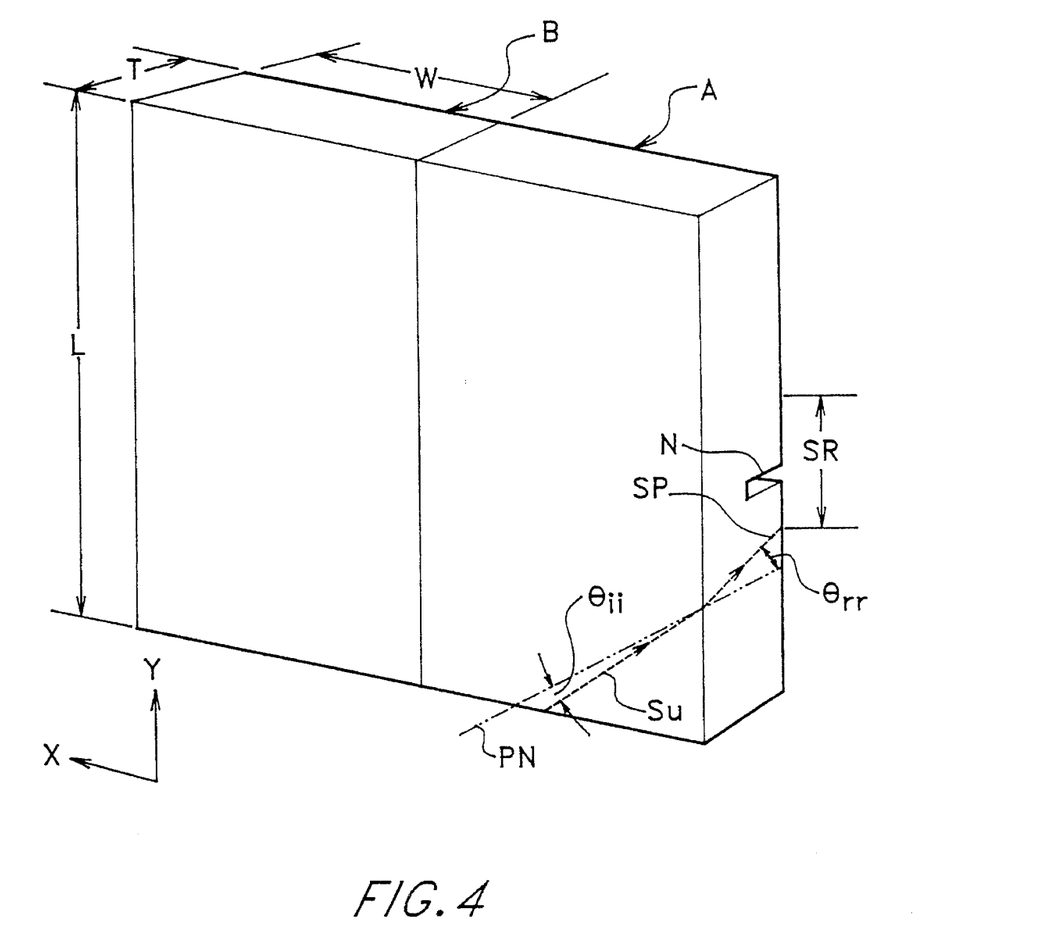
FIG. 4 is an orthogonal view of two specimens used in the feasibility demonstration of FIG. 2.

FIG. 4 shows the two surface-ground flat plates A, B used in the feasibility demonstration. Each is 114 mm (4.5 in) long L, 44 mm (1.75 in) wide W, and 13 mm (0.5 in thick T. In the experiment, the two specimens are arranged side-by-side as in FIG. 4. The two plates are identical except that they contain thin, surface-breaking notches N made by standard electro-discharge machining (EDM) procedures. The notch depths are 20% and 40% of the nominal plate thickness T (i.e., 2.5 mm (0.1 in) and 5.1 mm (0.2 in)).

The notches N have 0.3 mm (0.01 in.) mouth widths and traverse the entire width W of the plates A&B (i.e. 44 mm (1.75 in)). The probing ultrasonic signal $S_u$ is induced into the plate A or B at an incidence angle $\theta_{ii}$ relative to the plate normal PN. The ultrasonic signal SP in the plate will then be at an angle $\theta_{rr}$ relative to plate normal PN according to "Snell's Law" for shear wave signals. To achieve the test results to follow the ultrasonic signal SP was scanned over the shear range SR shown in FIG. 4.

EXPERIMENTAL APPROACHES

The following discussions of FIGS. 5, 6, 7, 8, 9 refer to the data from the experiment of FIG. 2. Therefore, the following discussions will contain references to FIG. 2 as well as FIGS. 5, 6, 7, 8, or 9.

In principle, the experimental arrangement shown in FIG. 2 is useful for measuring the thickness of the plate 16, finding delaminations in the plane of the plate 16, and detecting vertical cracks in the plate 16. Plate-thickness d2 measurements and delamination detection are best made using longitudinal-wave signals that propagate along the plate-surface normal NP. Such signals result from compressional-wave signals in the gas that propagate in the plate-surface NP normal direction. On the other hand, vertical-crack detection is best accomplished with longitudinal or shear-wave signals that propagate at an angle $\theta_r$ with respect to the plate-surface normal NP. To generate such signals, the symmetry axis of the pulse-echo transducer 15 must rotate in the sagittal plane to satisfy Snell's Law for either longitudinal or shear-wave signals. Because sound propagates much more slowly in a gas than in water, 300–500 m/s vs. 1500 m/s, the incidence angle $\theta_i$ of the ultrasonic probe 15 is correspondingly smaller. Furthermore, sensitivity to misalignment is greater for a gas-coupled system. Therefore, achieving proper initial transducer alignment with respect to the plate-surface normal NP becomes very important.

To prepare the system for experimental work, we typically first align the transducer 15 symmetry axis along the plate-surface normal NP at atmospheric pressure. The gas GG pressure is then increased to the desired working level, typically 6.9 MPa (1000 psi). (Increasing the gas GG pressure greatly improves the signal-to-noise (S/N) performance of the experimental system, making further adjustments very easy.) Next, we probe the spatial characteristics of the ultrasonic signals in the plate 16 using the small pin transducer, 24 as shown in FIG. 2. Finally, we align the transducer 15 symmetry axis to maximize the level of the front-surface reflection signal.

TRANSDUCER ALIGNMENT PROCEDURE

Figure 5A:
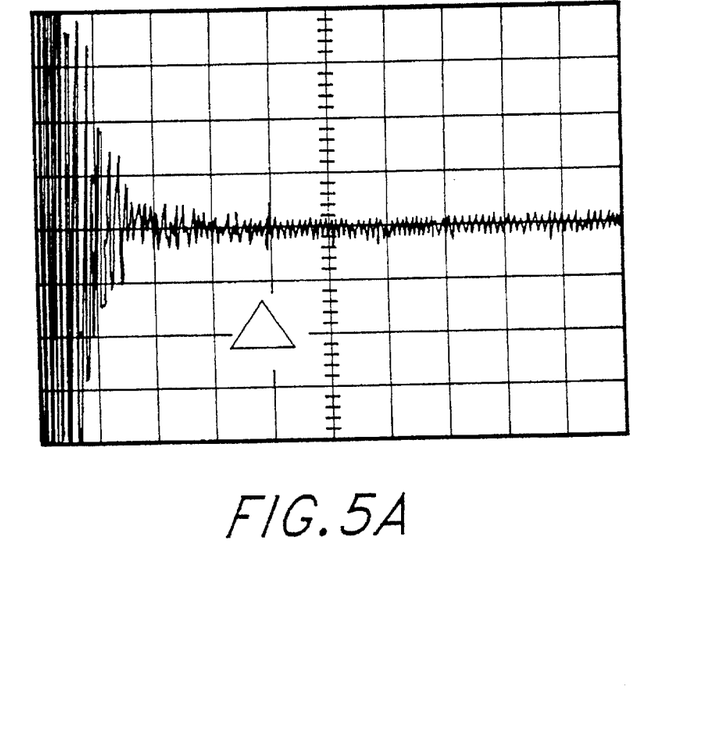
FIG. 5a is an oscilloscope trace of the return from the pulse-echo sensor of FIG. 2 illustrating the effect of atmospheric air pressure on the signal to noise performance of the sensor.

FIG. 5a is an oscilloscope 20 trace of an ultrasonic signal observed using atmospheric air (1500 m above sea level). The transducer 15 symmetry axis, of the experiment in FIG. 2, is along the plate-surface normal NP. Here, the front surfaces of the transducer 15 and the plate 16 are approximately 34 mm (1.3 in) apart. In FIG. 5a, a triangular marker Δ points to the location of the front-surface reflection signal, at 185 μs.

Figure 5B:
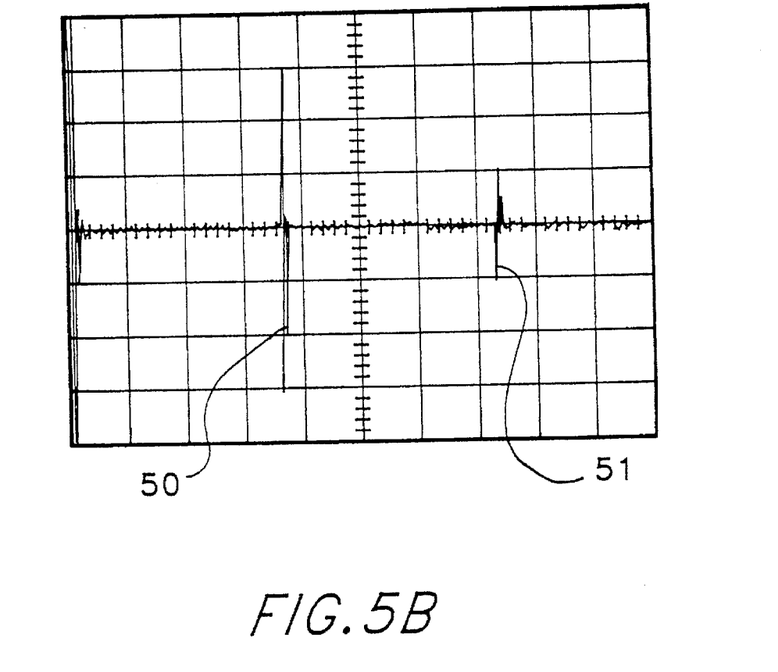
FIG. 5b is an oscilloscope trace of the return from the pulse-echo sensor of FIG. 2 illustrating the effect of increasing the density, by increasing the pressure, of the gas couplant on the signal to noise performance of the sensor. The environment is nitrogen at a pressure of 6.9 MPa (1000 psi).

FIG. 5b is the same ultrasonic signal appearing in FIG. 5a after increasing the pressure of the coupling gas GG (nitrogen) to approximately 6.9 MPa (1000 psi). The gain of the receiver amplifier 19 is decreased for the increased pressure of the coupling gas by 52 dB. The first signal 50, corresponds to the direct front-surface reflection. A second signal 51, corresponds to the second reverberation between the transducer 15 and plate 16, is apparent at 370 µs. The two signals emerge clearly from the noise. The signal-to-noise performance of the feasibility demonstration improves very rapidly with increased gas pressure and the second reverberation becomes clearly observable even at 0.3 MPa (40 psi). At this point, the final alignment of the transducer 15 symmetry axis with the plate-surface normal NP is possible.

To generate longitudinal and shear-wave signals at an angle with respect to the plate-surface normal NP, we rotate the symmetry axis of the pulse-echo transducer 15 in the sagittal plane. We then use the pin transducer 24 to learn the spatial and signal-to-noise characteristics of the resultant ultrasonic beams.

Figure 6A:
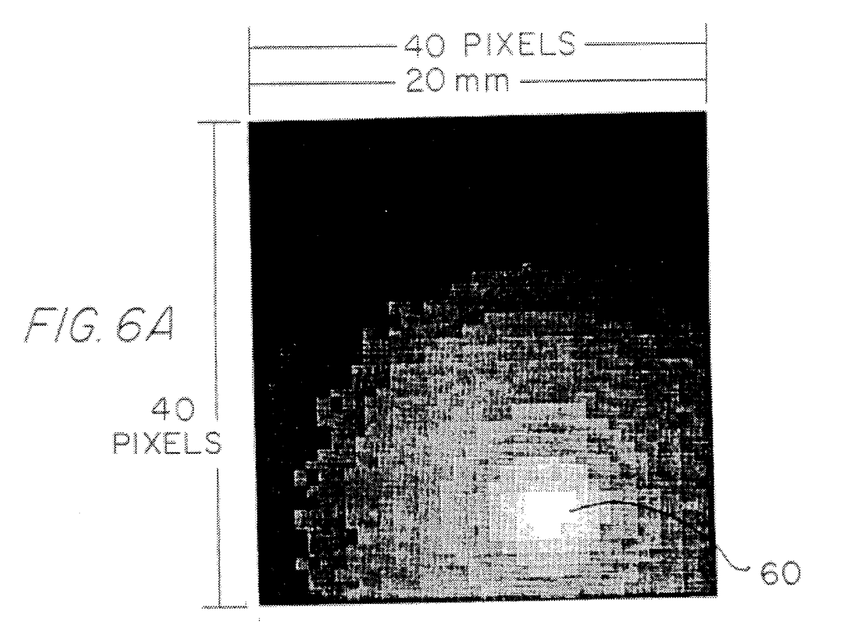
FIG. 6a is an oscilloscope scan from the back face sensor of FIG. 2. The scan is of the ultrasonic signal passing through the sample plate with the transmitter at a normal angle.
Figure 6B:
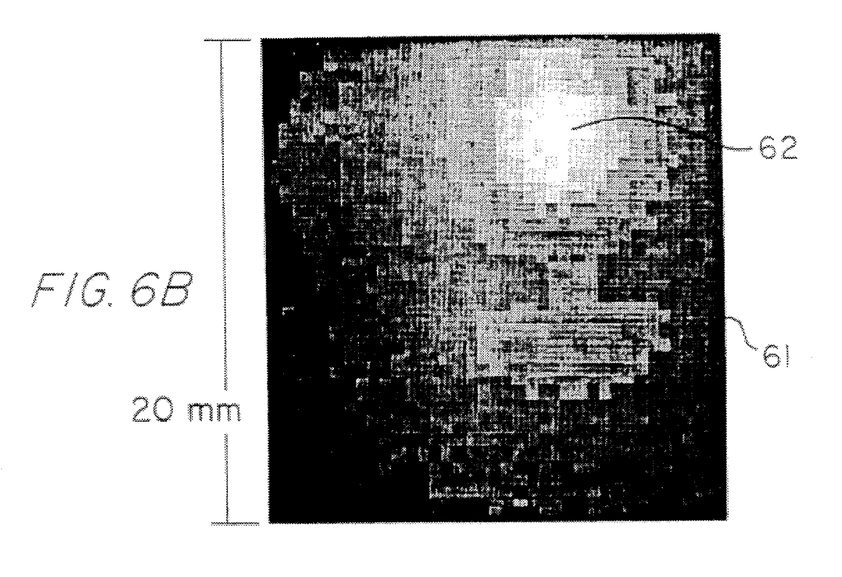
FIG. 6b is an oscilloscope scan from the back face sensor of FIG. 2. The scan is of the ultrasonic signal passing through the plate with the transmitter at 2.5° which produces a longitudinal wave at 45° and a shear wave at 23° inside the steel plate.

FIG. 6a and FIG. 6b are a pixel array found by probing the ultrasonic signals from the back side of the steel plate 16 of FIG. 2. The signal is transmitted through 8 mm of atmospheric air and 13 mm of steel plate 15. Each scan region is 20 mm on a side. The scan region is made up of an array of pixels 0.5 mm square. The "6-dB-down" points are about 5 mm from beam center.

FIG. 6a shows the ultrasonic signal 60 directed through the steel plate 15 on the axis normal NP to the plate 15.

FIG. 6b shows the signal detected at the back of the steel plate 15 when the angle of incidence $\theta_i$ is 2.5° producing a 45° longitudinal signal 62 and a 23° shear wave signal 61 inside the plate 15.

WALL THICKNESS DETERMINATION

Figure 7:
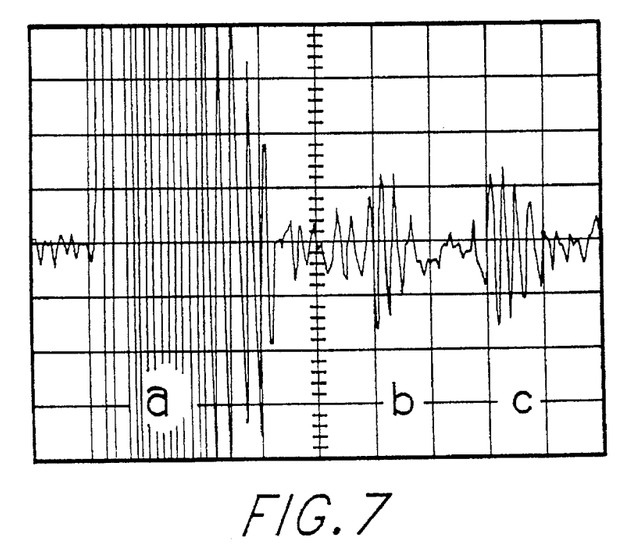
FIG. 7 is an oscilloscope trace of an echo return from the pulse echo sensor of FIG. 2. The trace shows the reflection from the front face of the steel plate, and two longitudinal wave reverberations within the steel plate.

FIG. 7 is a typical result of the experiment of FIG. 2 wherein the gage pressure is 6.9 MPa (1000 psi), the gas path is 38 mm (1.5 in), the plate 15 thickness d2 is 12.7 mm (0.5 in) and the amplifier 19 gain is 64 dB.

FIG. 7 is the oscilloscope trace from the pulse echo transducer 15. The direct reflection off the front surface of the plate 15 is shown at a. The following signals are multiple reverberations within the plate 15 b and c. The separation between the ultrasonic reverberations in the flat plate b and c is approximately 4 µs, consistent with the nominal plate thickness d2 of 13 mm (0.5 in). Measurement of the time separation between successive reverberations indicates the thickness of the plate and the presence of delaminations.

DETECTION OF SIMULATED VERTICAL CRACKS

Figure 8:
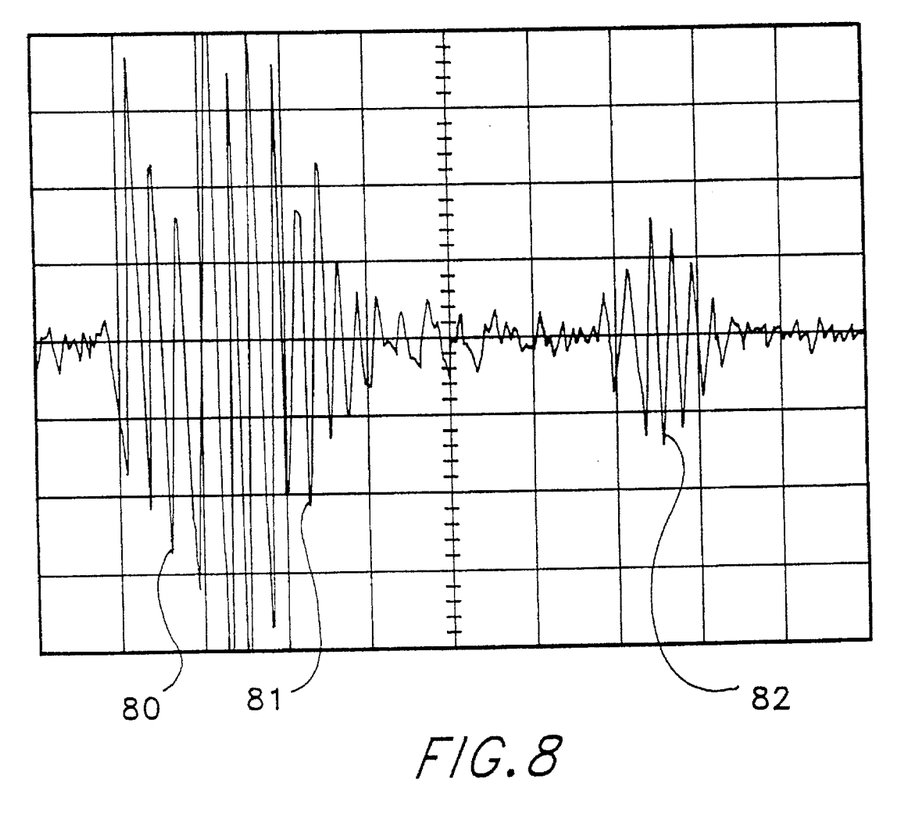
FIG. 8 is an oscilloscope trace of an echo return from the pulse echo sensor of FIG. 2. The trace shows the reflection from front surface of the plate and a 45° shear wave reflection from an EDM notch that is 40% of the thickness of the plate.

In principle, both longitudinal and shear-wave signals are useful in a pulse-echo configuration for flaw detection. In water-coupled systems, longitudinal-wave signals are preferable. Although, in our experiments, we observed both longitudinal and shear-wave flaw signals, we found that the shear-wave signals clearly separate from the front-surface reflection signals. The oscilloscope 20 trace in FIG. 8 is an illustration of this effect. The longitudinal-wave flaw signal 81 occurs at only 6 µs after the first observable front-surface reflection 80. Although we can detect the presence of the vertical crack (40% of wall thickness) by monitoring the behavior of the interferences between the two signals, the process is not reliable. On the other hand, the shear-wave reflections 82 arrive at approximately 11 µs following the beginning of the front-surface reflection and are clearly discernible.

Figure 9A:
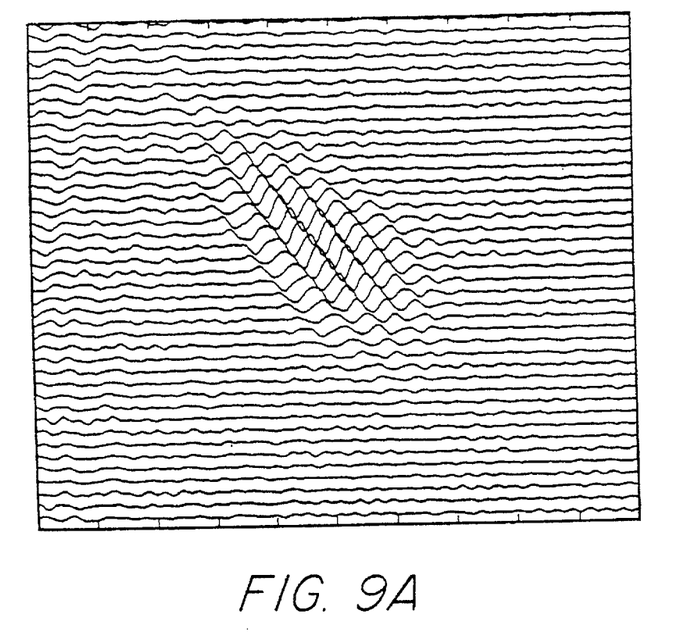
FIG. 9a is a trace array scan from the pulse echo sensor of FIG. 2. The scan is of a specimen of steel plate with a notch that is 20% of the plate thickness on the back surface of the plate.
Figure 9B:
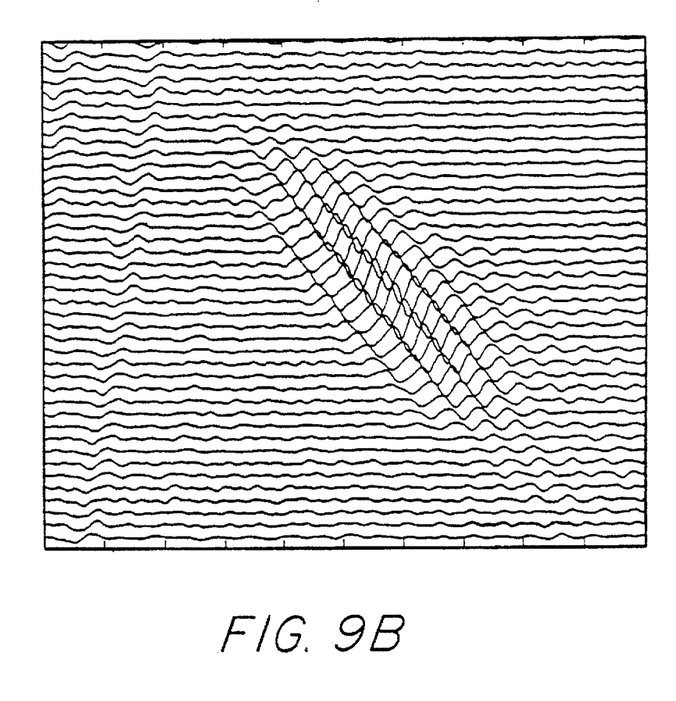
FIG. 9b is a trace array scan from the pulse echo sensor of FIG. 2. The scan is of a specimen of steel plate with a notch that is 40% of the plate thickness.

FIG. 9a and FIG. 9b are a scan of a notch 26 in the steel plate 16 of FIG. 2 using a shear wave signal refracted at an angle of refraction $\theta_r$ of 45° in the plate. The notch 26 is positioned in the middle of the 20 mm scan. The scan step size was 0.5 mm, the gage pressure for the nitrogen atmosphere was 6.8 MPa (980 psi). The distance between the transducer face and the front surface of the steel plate was 38 mm.

FIG. 9a and FIG. 9b are two scans obtained by moving the pulse-echo transducer 15 in the sagittal plane of the plate 16 of FIG. 2. These show the shear-wave reflections from vertical notches 26 with depths of 20% in FIG. 9a and 40% in FIG. 9b of the wall thickness. Waveform averaging (8 times) improved the signal-to-noise characteristics of the displayed signals. The data in FIGS. 8, 9a and 9b demonstrate the feasibility of using a gas-coupled, pulse-echo approach to detect flaws 26 and measure wall thickness d2 in plate geometries.

PRACTICAL IMPLEMENTATION OF THE INVENTION

Figure 10:
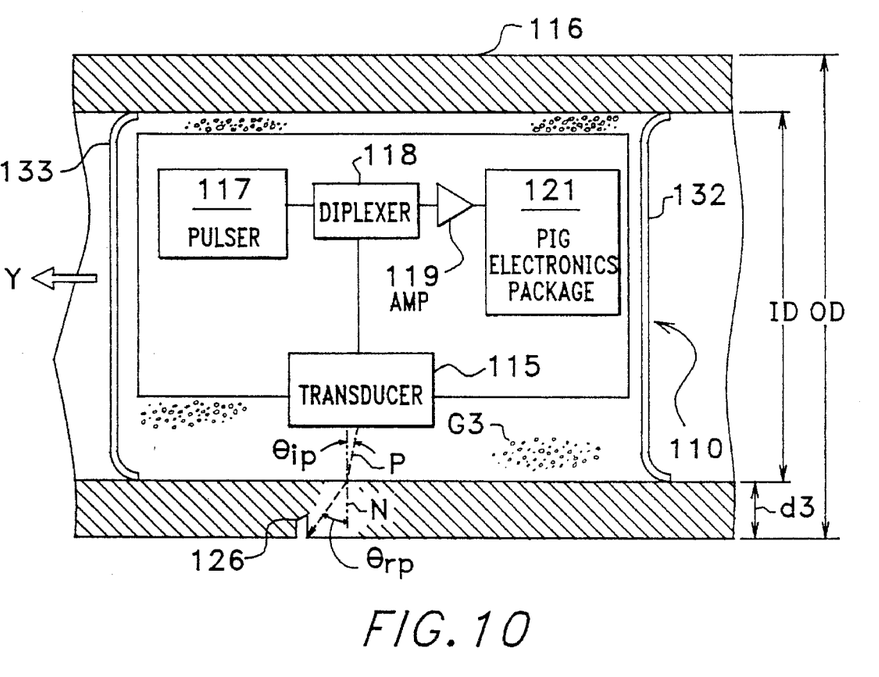
FIG. 10 is a cross section of a natural gas pipeline containing a schematic representation of an instrumentation pig utilizing the method of this invention.

FIG. 10 shows a block diagram of the invention implemented on an inspection pig 110 or robot 110 equipped with seals 132, 133 to propel the pig 110 or robot 110 through the pressurized natural gas pipeline 116 or pressure vessel 116 in the direction of flow $Y_p$. The pulser 117 operates through the diplexer 118 to project a high power ultrasonic pulse P into the steel pipeline 116 through the natural gas G3. The ultrasonic pulse P is projected from the pulse-echo transducer 115 at an angle of incidence $\theta_{ip}$ to the pipeline normal N. The angle of incidence $\theta_{ip}$ can be 0° for measuring the pipeline 116 wall thickness d3 and for detecting delamination or scaling flaws (not shown). For detecting cracks 126 or flaws 126 normal to the pipeline 116 the angle of incidence $\theta_{ip}$ of the ultrasonic pulse P will be such that the angle of refraction $\theta_{rp}$ in the steel pipeline 116 is 45° to the pipeline normal N. The small echo reflected off of the outside diameter OD of the steel pipeline 116 or off of flaws 126 in the pipeline 116 will be directed back to the pulse-echo transducer 115. The small electrical signal from the pulse echo will go from the pulse-echo transducer 115 through the diplexer 118 to the amplifier 119. The combination of the diplexer 118 and the amplifier 119 form a circuit with an extremely large dynamic range. Whereby the amplifier 119 can survive the large electrical pulse P going to the pulse-echo transducer 115, recover from saturation, receive the small echo signal, and amplify it to a level suitable for use by the next stage.

The above approach will also allow the use of this method to be used on oil pipelines that have large gas bubbles (i.e. at the top of a hill). This method would continue to get good data when the gas is encountered.

The output of the amplifier now goes to the pig electronics package 121 for signal processing and storage. The pig electronics package 121 contains the processing, storage, and power required to maintain the pig during its travel through the pipeline 116.

The invention as shown in FIG. 10 can also be used on a robot 110 in a plastic, ceramic, or steel (including stainless steel) pipeline or pressure vessel 116.

Although the present invention has been described with reference to preferred embodiments, numerous modifications and variations can be made and still the result will come within the scope of the invention. No limitation with respect to the specific embodiments disclosed herein is intended or should be inferred.

I claim:

1. A method for determining a pressure vessel wall thickness and detecting a flaw in the pressure vessel wall comprising the steps of:

generating a high power electrical pulse with a pulser;

transmitting the high power electrical pulse through a diplexer and then simultaneously to an ultrasonic transducer which is located inside the pressure vessel, and to an amplifier;

transmitting an ultrasonic pulse from the ultrasonic transducer through a pressurized gas couplant and then into an inside surface of the pressure vessel;

receiving through the ultrasonic transducer, the diplexer, and the amplifier a return signal from the inside surface of the pressure vessel and calculating the distance d1 from the transducer to the inside surface;

receiving through the ultrasonic transducer, the diplexer, and the amplifier a return signal from an outside surface of the pressure vessel;

calculating a thickness of the pressure vessel wall; detecting a flaw in the pressure vessel wall; choosing said pressure vessel from a group of gas pipelines having a gas pipeline wall and a composition of metal, plastic, and ceramic;

said combination of the amplifier and the diplexer forming a circuit having a large dynamic range, a fast response, and a fast recovery; and selecting the diplexer to comprise a means for producing a saturation threshold matched to the input voltage limits of the amplifier.

2. The method of claim 1 further comprising the step of characterizing the flaw by processing multiple return signals from inside the gas pipeline wall.

3. The method of claim 1 further comprising the steps of:

mounting the ultrasonic transducer at a small incidence angle relative to a normal angle in reference to the wall of the pipeline, thereby creating an angle of refraction of the ultrasonic pulse inside the wall of the pipeline; and using the ultrasonic pulse at the angle of refraction inside the wall of the pipeline to detect a flaw within the wall of the pipeline.

4. The method of claim 1 further comprising the step of mounting in a pig, the pulser, the diplexer, the ultrasonic transducer, and the amplifier.

5. An apparatus for determining a pressure vessel wall thickness and detecting a flaw in the pressure vessel wall comprising;

means for generating a high power electrical pulse;

means for transmitting the high power electrical pulse through a diplexer and then simultaneously to an ultrasonic transducer which is located inside the pressure vessel and to an amplifier;

means for transmitting an ultrasonic pulse from the ultrasonic transducer through a pressurized gas couplant and then into an inside surface of the pressure vessel;

means for receiving through the ultrasonic transducer, the diplexer, and the amplifier a return signal from the inside surface of the pressure vessel and calculating a distance d1 from the transducer to the inside surface;

means for receiving through the ultrasonic transducer, the diplexer, and the amplifier a return signal from an outside surface of the pressure vessel;

means for calculating a thickness of the pressure vessel wall;

means for detecting a flaw in the pressure vessel wall;

said pressure vessel is chosen from a group of metal, plastic, and ceramic pressure vessels;

said pressure vessel further comprises a gas pipeline having a gas pipeline wall;

said means for generating a high power electrical pulse further comprises a pulser; and said diplexer further comprises a means for producing a saturation threshold matched to the input voltage limits of the amplifier.

6. The apparatus of claim 5, wherein the amplifier further comprises a large dynamic range, a fast response, and a fast recovery.

7. The apparatus of claim 5, wherein the means for calculating a thickness of a gas pipeline wall further comprises a power supply, a storage device, and a processing module.

8. The apparatus of claim 5 further comprising a means for detecting and characterizing the flaw by processing multiple return signals from inside the gas pipeline wall.

9. The apparatus of claim 5 further comprising:

means for mounting the ultrasonic transducer at a small incidence angle relative to a normal angle in reference to the wall of the pipeline, thereby creating an angle of refraction of the ultrasonic pulse inside the pipeline wall; and means for using the ultrasonic pulse at the angle of refraction inside the gas pipeline wall to detect a flaw within the gas pipeline wall.

10. The apparatus of claim 5 further comprising a pig housing means for the pulser, the diplexer, the ultrasonic transducer, the amplifier, and the means for calculating.

11. The apparatus of claim 5, wherein the flaw further comprises a location on the outside surface of the pressure vessel wall.

* * * * *